United States Patent
Li (10) Patent No.: US 12,358,146 B2
(45) Date of Patent: Jul. 15, 2025

(54) CALIBRATION METHOD, MECHANICAL ARM CONTROL METHOD, AND SURGICAL SYSTEM

(71) Applicants: BEIJING HURWA ROBOT MEDICAL TECHNOLOGY CO., LTD., Beijing (CN); BEIJING HURWA ROBOT TECHNOLOGY CO., LTD., Beijing (CN)

(72) Inventor: Shugang Li, Beijing (CN)

(73) Assignees: BEIJING HURWA ROBOT MEDICAL TECHNOLOGY CO., LTD., Beijing (CN); BEIJING HURWA ROBOT TECHNOLOGY CO., LTD., Beijing (CN)

( * ) Notice: Subject to any disclaimer, the term of this patent is extended or adjusted under 35 U.S.C. 154(b) by 327 days.

(21) Appl. No.: 17/721,953

(22) Filed: Apr. 15, 2022

(65) Prior Publication Data
US 2022/0234206 A1  Jul. 28, 2022

Related U.S. Application Data (63) Continuation of application No. PCT/CN2021/109409, filed on Jul. 29, 2021.

(30) Foreign Application Priority Data

Nov. 7, 2020 (CN) .......................... 202011235567.9
Jan. 27, 2021 (CN) .......................... 202110113527.5

(51) Int. Cl.
B25J 9/16  (2006.01)
A61B 34/20  (2016.01)
(Continued)

(52) U.S. Cl.
CPC ............. *B25J 9/1692* (2013.01); *A61B 34/20* (2016.02); *A61B 34/30* (2016.02); *B25J 13/089* (2013.01);
(Continued)

(58) Field of Classification Search
CPC ....... B25J 9/1692; B25J 13/089; A61B 34/20; A61B 34/30; A61B 2017/00725;
(Continued)

(56) References Cited

U.S. PATENT DOCUMENTS

2004/0251866 A1* 12/2004 Gan ...................... B25J 9/1692
                                                        318/568.11
2004/0254677 A1* 12/2004 Brogardh ............. G05B 19/425
                                                        700/250
(Continued)

FOREIGN PATENT DOCUMENTS

CN    107898501 A    4/2018
CN    109129445 A    1/2019
(Continued)

OTHER PUBLICATIONS

The Notice of Reasons for Refusal for Japanese Patent Application No. 2022-527216, dated May 23, 2023.
(Continued)

*Primary Examiner* — Abby Y Lin
*Assistant Examiner* — Karston G. Evans (57) ABSTRACT

Embodiments of the present application provide a calibration method, a mechanical arm control method, and a surgical system for calibrating an angle of a target feature structure installed on an end of the mechanical arm. The calibration method includes: setting a moving path of the end and controlling the end to move along the moving path, the moving path including at least three position points that are not located on a same straight line; obtaining a first
(Continued)

position of the moving path of the end in an absolute coordinate system; obtaining a second position of the target feature structure in the absolute coordinate system; and determining a relative positional relationship between the target feature structure and a mechanical arm end coordinate system according to the first position, the second position and a predetermined third position of the moving path in the mechanical arm end coordinate system.

11 Claims, 6 Drawing Sheets

(51) Int. Cl.
  *A61B 34/30* (2016.01)
  *B25J 13/08* (2006.01)
  *A61B 17/00* (2006.01)
  *A61B 90/00* (2016.01)
(52) U.S. Cl.
  CPC ............... *A61B 2017/00725* (2013.01); *A61B 2034/2055* (2016.02); *A61B 2034/2059* (2016.02); *A61B 2090/3983* (2016.02)
(58) Field of Classification Search
  CPC .... A61B 2034/2055; A61B 2034/2059; A61B 2090/3983; A61B 34/77; A61B 34/70; A61B 34/10; A61B 2034/101
  See application file for complete search history.

(56) References Cited

U.S. PATENT DOCUMENTS

| 2009/0118864 | A1* | 5/2009 | Eldridge | B25J 9/1692 901/29 |
| 2017/0322010 | A1* | 11/2017 | Mu | G01B 21/042 |
| 2021/0106342 | A1* | 4/2021 | Blackwell | A61B 90/361 |
| 2022/0008137 | A1* | 1/2022 | Brik | A61B 34/30 |
| 2022/0097234 | A1* | 3/2022 | Huang | B25J 9/1692 |
| 2022/0250248 | A1* | 8/2022 | He | G06T 7/73 |

FOREIGN PATENT DOCUMENTS

| CN | 109249392 A | 1/2019 |
| CN | 110811834 A | 2/2020 |
| CN | 110815203 A | 2/2020 |
| CN | 110974426 A | 4/2020 |
| CN | 111037561 A | 4/2020 |
| CN | 111590593 A | 8/2020 |
| CN | 112932670 A | 6/2021 |
| DE | 102012209769 A1 | 12/2013 |
| EP | 1120204 A2 | 8/2001 |
| JP | 2014-180720 A | 9/2014 |
| JP | 2018-514394 A | 6/2018 |
| KR | 20180113512 A | 10/2018 |

OTHER PUBLICATIONS

The Communication from European Patent Office dated Nov. 30, 2023 for Application No. 21876734.1.
Request for the Submission of an Opinion from Korean Intellectual Property Office dated Jan. 18, 2024 for Application No. 10-2022-7012734.
The first examination opinion dated Jul. 30, 2021 for Chinese application No. 202110113527.5.
The second examination opinion dated Nov. 18, 2021 for Chinese application No. 202110113527.5.
International Search Report dated Sep. 28, 2021 for PCT application No. PCT/CN2021/109409.
Request for the Submission of an Opinion dated Jul. 8, 2024 for Korean Patent Application No. 10-2022-7012734.

* cited by examiner

FIG. 3 setting a moving path of the end of the mechanical arm and controlling the end of the mechanical arm to move along the moving path — S101 obtaining a first position of the moving path of the end of the mechanical arm in an absolute coordinate system — S102 obtaining a second position of the target feature structure in the absolute coordinate system — S103 determining a relative positional relationship between the target feature structure and a mechanical arm end coordinate system according to the first position, the second position and a predetermined third position of the moving path in the mechanical arm end coordinate system — S104

CALIBRATION METHOD, MECHANICAL ARM CONTROL METHOD, AND SURGICAL SYSTEM

CROSS REFERENCE TO RELATED APPLICATIONS

The present application is a continuation of PCT Application No. PCT/CN2021/109409, which is filed on Jul. 29, 2021 and claims priority to Chinese Patent Application No. 202011235567.9 titled by "CALIBRATION METHOD AND SYSTEM" and filed on Nov. 7, 2020, and Chinese Patent Application No. 202110113527.5 titled by "CALIBRATION METHOD, MECHANICAL ARM CONTROL METHOD AND SURGICAL SYSTEM" and filed on Jan. 27, 2021, all of which are incorporated herein by reference in their entireties.

TECHNICAL FIELD

The present application belongs to the technical field of computer-assisted surgery, and in particular relates to a calibration method, a mechanical arm control method and a surgical system.

BACKGROUND

In a surgical operation, in order to ensure the effect of the operation, for example, it is necessary to calibrate an angle of a target feature structure (such as a medical device) that performs an operation task. Taking a knee replacement surgery as an example, for example, an angle of a medical device needs to be calibrated before surgery to ensure that the cutting plane of the medical device can be consistent with the osteotomy plane during the surgery. Otherwise, once there is a deviation between the two planes, a prosthesis may be installed on the cut out plane with a bad effect, and even the prosthesis cannot be installed.

If one wants to calibrate the angle of the target feature structure, it is more important to determine a relative positional relationship between the target feature structure and the mechanical arm end coordinate system. The inventor of the present application found that, due to the affecting of machining errors and assembly errors of the target feature structure, the relative positional relationship between the target feature structure and the mechanical arm end coordinate system cannot be accurately determined by related technologies.

SUMMARY

The present application provides a calibration method, a mechanical arm control method and a surgical system, which can accurately determine the relative positional relationship between the target feature structure and the mechanical arm end coordinate system, and can be adapted to calibrate the angle of the target feature structure.

In a first aspect, the embodiments of the present application provide a calibration method for calibrating an angle of a target feature structure installed on an end of a mechanical arm, the method including steps of:
 setting a moving path of the end and controlling the end to move along the moving path, the moving path including at least three position points that are not located on a same straight line;
 obtaining a first position of the moving path of the end in an absolute coordinate system;
 obtaining a second position of the target feature structure in the absolute coordinate system; and
 determining a relative positional relationship between the target feature structure and a mechanical arm end coordinate system according to the first position, the second position and a predetermined third position of the moving path in the mechanical arm end coordinate system.

In a second aspect, the embodiments of the present application provide a mechanical arm control method adapted to control a predetermined plane of the target feature structure installed on the end of the mechanical arm to align with a target plane, the control method includes steps of:
 calibrating an angle between the target feature structure and the end by the calibration method provided by the first aspect;
 setting a moving plane of the mechanical arm, so that the end can move in the moving plane when subjected to an external force in a predetermined direction, and the moving plane coincides with the predetermined plane of the target feature structure; and
 controlling the mechanical arm to move so as to align the predetermined plane with the target plane.

In a third aspect, the embodiments of the present application provide a surgical system including:
 a mechanical arm, an end of the mechanical arm being installed with a target feature structure; and
 a controller, programmed to:
 set a moving path of the end and control the end to move along the moving path, the moving path including at least three position points that are not located on a same straight line; and
 determine a relative positional relationship between the target feature structure and a mechanical arm end coordinate system based on an obtained first position of the moving path of the end in an absolute coordinate system, an obtained second position of the target feature structure in the absolute coordinate system and a predetermined third position of the moving path in the mechanical arm end coordinate system.

In a fourth aspect, the embodiments of the present application further provide a computer program product, wherein the program product is stored in a non-volatile storage medium, and the program product can be executed by at least one processor to implement the steps of the calibration method provided in one aspect or the mechanical arm control method provided in the second aspect.

In a fifth aspect, the embodiments of the present application further provide a storage medium, on which a program is stored, and when the program is executed, the steps of the calibration method provided by the first aspect or the mechanical arm control method provided by the second aspect are performed.

The calibration method, the mechanical arm control method and the surgical system of the embodiments of the present application can accurately determine the relative positional relationship between the target feature structure and the mechanical arm end coordinate system, and can be used to calibrate the angle of the target feature structure.

BRIEF DESCRIPTION OF THE DRAWINGS

In order to illustrate the technical solutions of the embodiments of the present application or related technologies more clearly, the accompanying drawings that need to be used in the descriptions of the embodiments or related technologies will be briefly introduced below; obviously, the accompanying drawings in the following descriptions are some embodiments of the present application, and for the person skilled in the art, other accompanying drawings can be obtained from these accompanying drawings without any creative effort.

DETAILED DESCRIPTION

Features and exemplary embodiments of various aspects of the present application will be described in detail below, and in order to make the purpose, technical solutions and advantages of the present application clearer, the present application will be described in further detail below in combination with the accompanying drawings and specific embodiments. It should be understood that the specific embodiments described herein are only intended to explain the present application, but not to limit the present application. It will be apparent to the person skilled in the art that the present application may be practiced without some of these specific details. The following description of the embodiments is merely to provide a better understanding of the present application by illustrating examples of the present application.

Reference throughout this document to "embodiments," "some embodiments," "one embodiment," or "an embodiment," etc., means that particular features, components, or characteristics described in connection with the embodiment is included in the at least one embodiment. Thus, the phrases "in various embodiments", "in some embodiments", "in at least another embodiment" or "in an embodiment", etc. throughout this specification are not necessarily all referring to the same embodiment. Further, the particular features, components or characteristics may be combined in any suitable manner in one or more embodiments. Thus, without limitation, particular features, components or characteristics illustrated or described in connection with one embodiment may be combined in whole or in part with features, components or characteristics of one or more other embodiments. Such modifications and variations are intended to fall within the scope of the present application.

It should be noted that in the present application, relational terms such as first and second, etc. are only used to distinguish one entity or operation from another entity or operation, and do not necessarily require or imply any such actual relationship or sequence between these entities or operations. Moreover, the terms "comprise", "include" or any other variation thereof are intended to encompass a non-exclusive inclusion such that a process, method, article or device that includes a list of elements includes not only these elements, but also includes other elements not explicitly listed or inherent to such a process, method, article or device. Without further limitations, an element defined by the phrase "comprises" does not preclude the presence of additional identical elements in the process, method, article or device that includes the element.

Before describing the technical solutions provided by the embodiments of the present application, in order to facilitate the understanding of the embodiments of the present application, the problems existing in the prior art are firstly described in detail below by taking a knee replacement surgery as an example.

Figure 1:
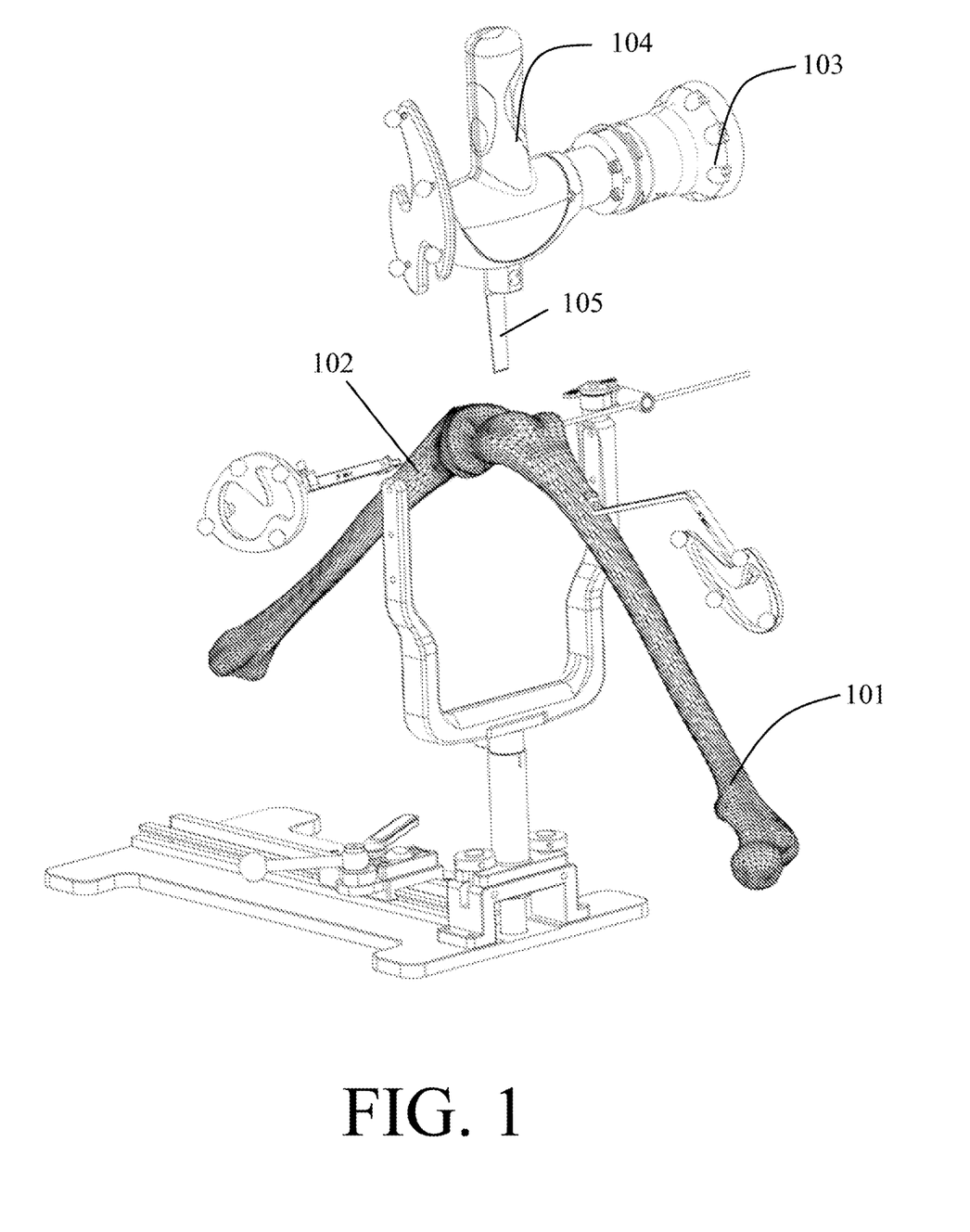
FIG. 1 is a schematic diagram of a scene of a knee replacement operation.

As shown in FIG. 1, where a knee replacement surgery is taken as an example, in the knee replacement surgery, it is generally necessary to remove a part of bones on a femur 101 and a tibia 102 to form a prosthesis fixing interface that fits with a prosthesis. The apparatus for cutting the bones may include, for example, the following components: a mechanical arm 103 and an actuator 104 fixedly connected to an end of the mechanical arm 103, wherein one end of the actuator 104 is carried with a medical device 105, and the medical device 105 may include a saw blade. During the surgery, the saw blade is driven by a motor in the actuator 104 and swings at high speed, so as to achieve the purpose of cutting the bones.

Figure 2:
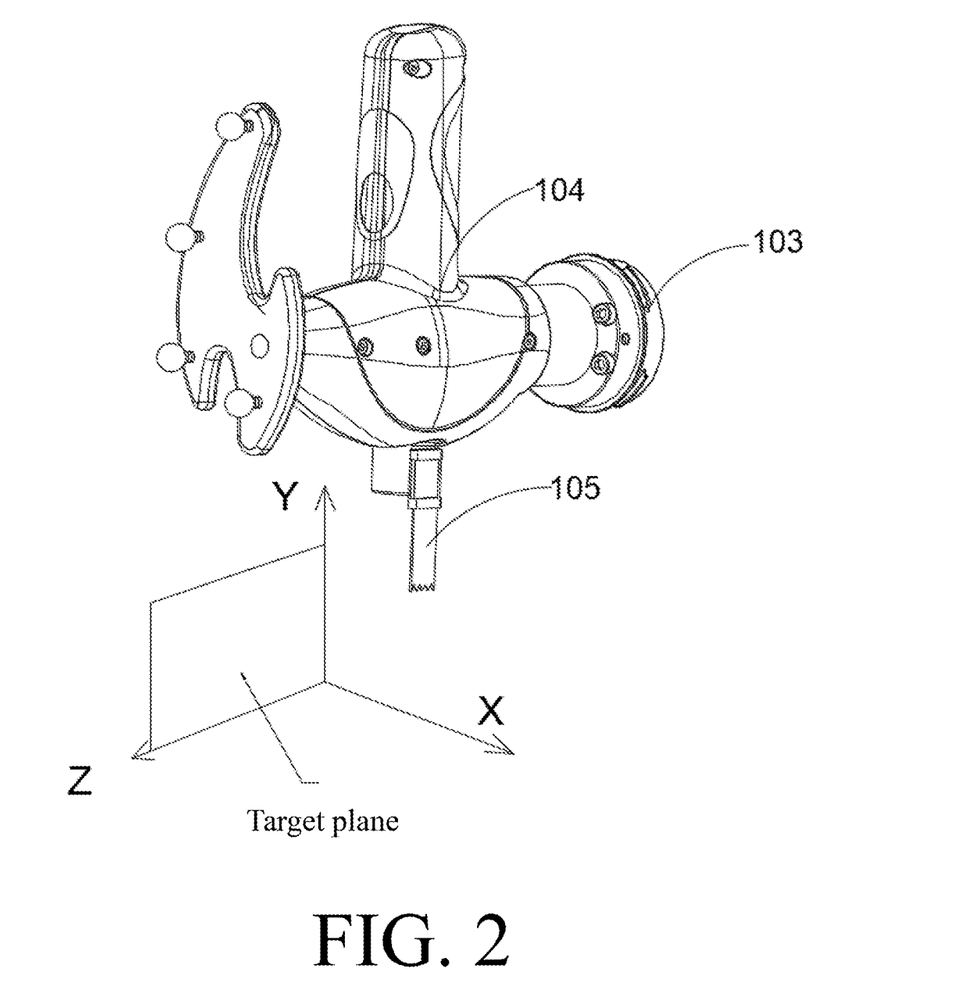
FIG. 2 schematically shows a moving plane and a target plane of an end of a mechanical arm.

As shown in FIG. 2, a moving plane of the end of the mechanical arm 103 can be defined by a manner of force feedback, so that the end of the mechanical arm 103 can be moved only in a plane parallel to a preset target plane (e.g., a prosthesis fixing interface), and thus, the medical device 105 will not shake in a first direction, thereby ensuring the cutting accuracy. Here, the first direction is a direction perpendicular to the target plane.

However, through the research by the inventor of the present application, it is found that in the related technologies, the actual working plane of the medical device is inconsistent with the planned target plane, the surgical accuracy is low, and the surgical effect is poor. In order to solve the above-mentioned technical problems, the inventor of the present application firstly conducted research on the root causes of the above-mentioned technical problems, and by the research, finally found that the root causes of the above-mentioned technical problems are as below.

In the related technologies, the moving plane of the end of the mechanical arm is set by taking a mechanical arm end coordinate system as a reference, and the processing errors and assembly errors of the medical device are ignored. Simply put, when designing the equipment where the mechanical arm and the medical device are located, a relative positional relationship between the medical device and the mechanical arm end coordinate system can be determined. Assuming that there is no processing errors and assembly errors relating to the medical device, the above technical problems will not occur if setting the moving plane of the end of the mechanical arm according to the relative positional relationship between the medical device and the mechanical arm end coordinate system in an ideal state. However, in fact, due to the limitation of the current processing accuracy and assembly accuracy, the processing errors and assembly errors relating to the medical device cannot be completely eliminated. Therefore, due to the existence of processing errors and assembly errors relating to the medical device, the relative positional relationship between the medical device and the mechanical arm end coordinate system cannot be determined accurately in the related technologies, or the relative positional relationship between the medical device and the mechanical arm end coordinate system determined by the related technologies has errors. Thus, when setting the moving plane of the end of the mechanical arm by reference to the relative positional relationship with errors, an angular deviation will be generated between the set moving plane of the end of the mechanical arm and the actual working plane of the medical device, which will lead to the inconsistency between the actual working plane of the medical device and the preset target plane, thereby resulting in the lower surgical accuracy, and the poor surgical effect.

Further, through research, the inventor of the present application found that when the moving plane of the end of the mechanical arm is inconsistent with the actual working plane of the medical device, the medical device would be subjected to a component force of a cutting resistance along a normal direction of the working plane in the feeding process, causing the problem that the medical device is easily bent or broken during feeding.

In view of the above findings, the embodiments of the present application provide a calibration method, a mechanical arm control method and a surgical system to solve the above technical problems.

Before introducing the calibration method provided by the embodiments of the present application, in order to facilitate the understanding of the embodiments of the present application, the surgical system of the embodiments of the present application is briefly described below at first.

Figure 3:
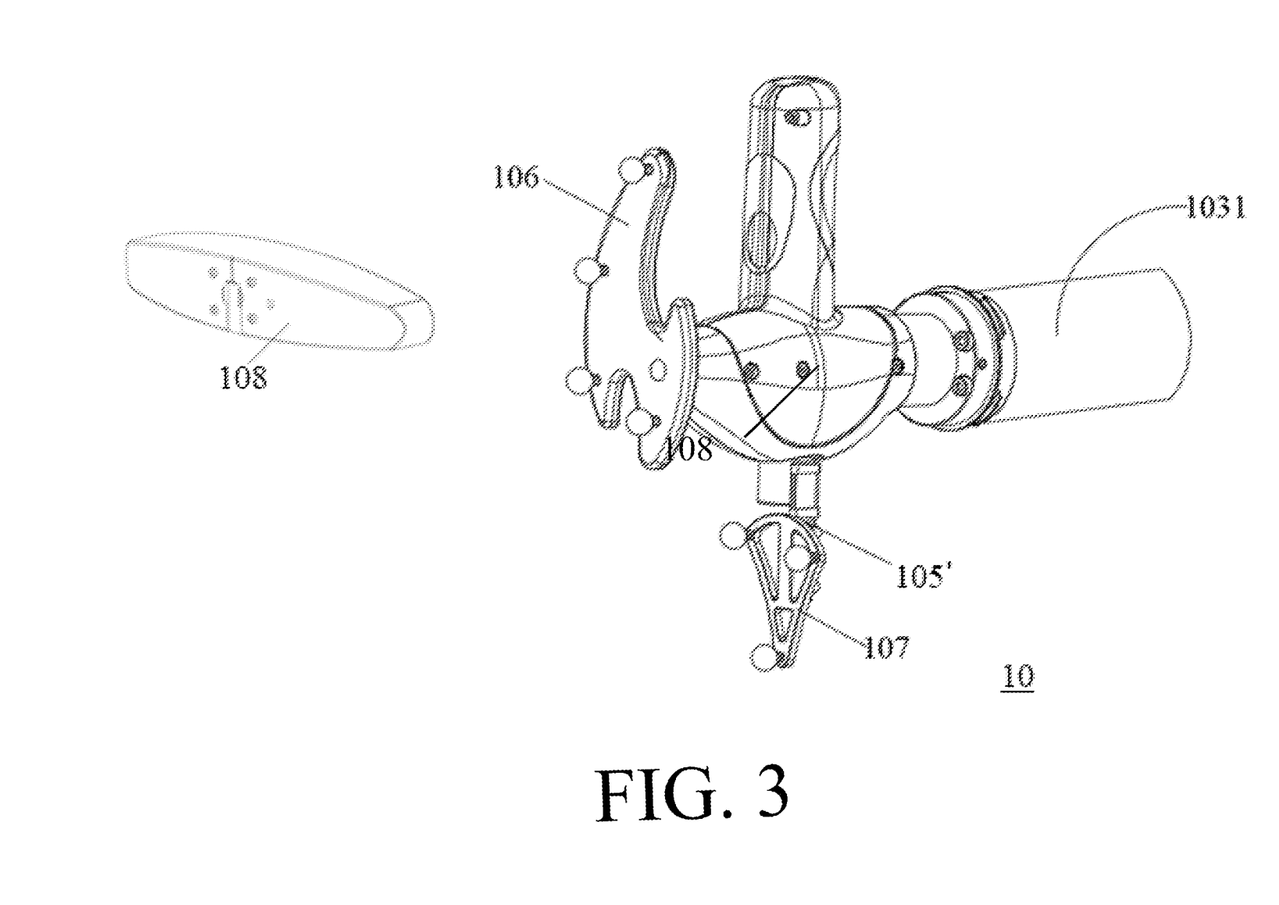
FIG. 3 schematically shows a surgical system according to an embodiment of the present application.

As shown in FIG. 3, the surgical system 10 includes: a mechanical arm (only an end 1031 of the mechanical arm is shown in the figure); a target feature structure 105' installed on the end 1031 of the mechanical arm, wherein the target feature structure 105' for example, may be a medical device, and the medical device may include a saw blade, or a cutter blade; and a controller (not shown in the figure), which can be programmed, for example, to execute the calibration method or the mechanical arm control method of the embodiments of the present application.

In order to achieve accurate positioning of the end 1031 of the mechanical arm and the target feature structure 105', as shown in FIG. 3, the surgical system 10 may further include: a first tracker 106 installed on the end 1031 of the mechanical arm; a second tracker 107, installed on the target feature structure 105'; and a localizer 108, adapted to obtain spatial orientation information of the first tracker 106 and the second tracker 107.

It should be noted that the structure and size of each component of the surgical system 10 as shown in FIG. 3 are only schematic, and can be flexibly adjusted according to actual conditions, and the present application is not limited thereto. In the embodiments of the present application, the mechanical arm may be a multi-axis mechanical arm, and the end 1031 of the mechanical arm may be the Nth axis of the multi-axis mechanical arm, wherein N is a positive integer.

The calibration method of the embodiments of the present application is introduced as below.

Figure 4:
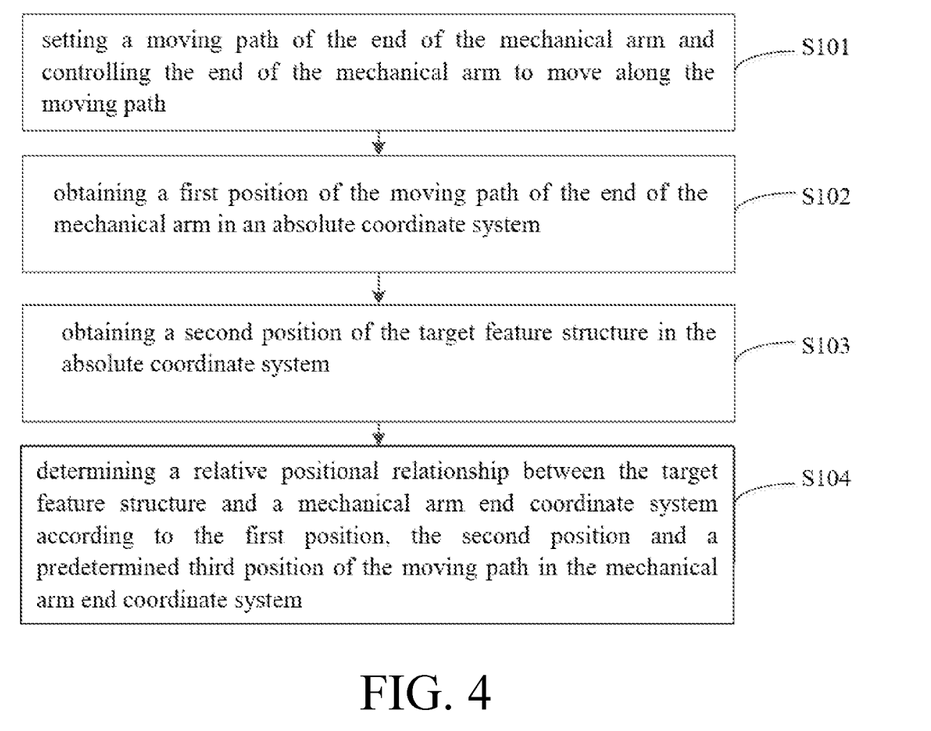
FIG. 4 is a schematic flowchart of a calibration method provided by an embodiment of the present application.

FIG. 4 is a schematic flowchart of the calibration method provided by the embodiments of the present application. As shown in FIG. 4, the method may include the following step:

step S101, setting a moving path of the end of the mechanical arm and control the end of the mechanical arm to move along the moving path.

Figure 5:
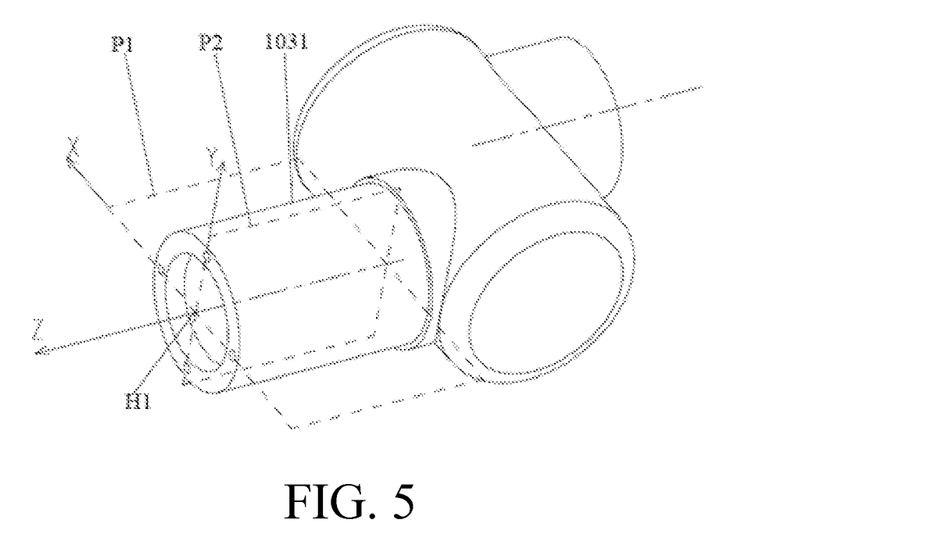
FIG. 5 schematically shows a mechanical arm end coordinate system according to an embodiment of the present application.

As shown in FIG. 5, in order to facilitate the control of the movement of the end 1031 of the mechanical arm, a mechanical arm end coordinate system H1 is established on the end 1031 of the mechanical arm. When controlling the end 1031 of the mechanical arm to move, a control command can be sent to a device that drives the end 1031 of the mechanical arm to move, the control command takes the mechanical arm end coordinate system H1 as basis, and is adapted to instruct a movement amount and/or a rotation angle relative to the mechanical arm end coordinate system H1, and for example, the control command may instruct the end 1031 of the mechanical arm to translate two units along a first coordinate axis (e.g., x-axis) of the mechanical arm end coordinate system H1 and/or rotate by a certain angle, so as to achieve the accurate control of the movement and/or rotation of the end 1031 of the mechanical arm.

Figure 6:
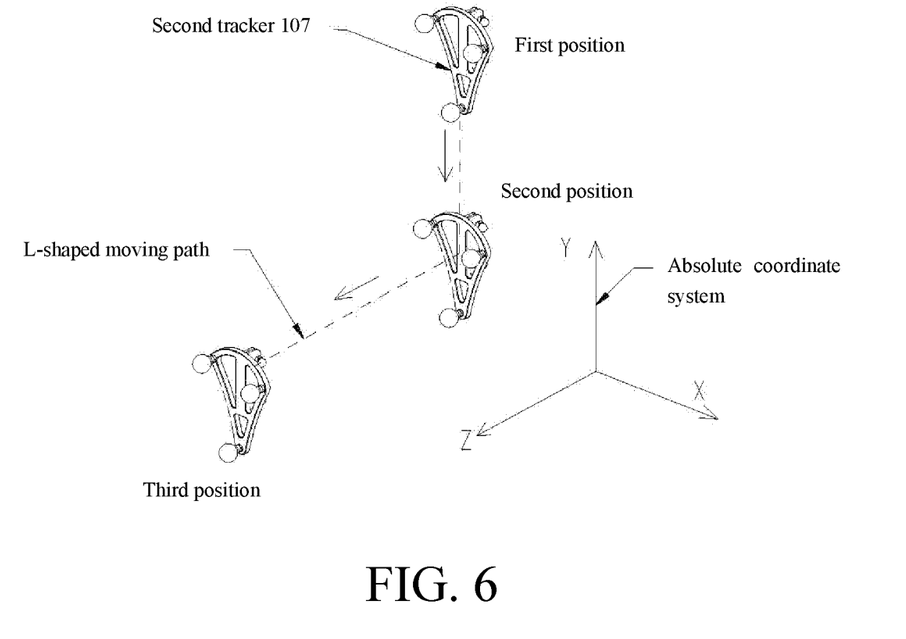
FIG. 6 schematically shows a moving path of a second tracker according to an embodiment of the present application.

In some embodiments, the moving path of the end 1031 of the mechanical arm (hereinafter referred to as the mechanical arm end 1031) may be preset, and in order to facilitate the determination of a first position of the moving path in an absolute coordinate system, the moving path may include at least three position points that are not located on a same straight line, that is, the moving path is a non-straight line path. The non-straight line path may include a polyline path or a curved path. As shown in FIG. 6, referring to a moving trajectory of the second tracker 107, the polyline path can be an "L-shaped moving trajectory" or "L-shaped moving path", that is, the straight-line path from the first position to the second position and the straight-line path from the second position to the third position are perpendicular to each other and form an "L shape". It is easy to understand that the non-straight line path may further include an acute-angle path or an obtuse-angle path, the acute-angle path may be a path with an acute angle formed between the straight-line path from the first position to the second position and the straight-line path from the second position to the third position, and the obtuse-angle path may be a path with an obtuse angle formed between the straight-line path from the first position to the second position and the straight-line path from the second position to the third position.

The method further includes step S102, obtaining the first position of the moving path of the end of the mechanical arm in the absolute coordinate system.

Specifically, during the movement of the mechanical arm end 1031 along the moving path, the first position of the moving path of the mechanical arm end 1031 in the absolute coordinate system may be obtained. In some embodiments, for example, the first position of the moving path in the absolute coordinate system can be obtained by tracking the tracker directly or indirectly connected to the end of the mechanical arm by use of a localizer. The tracker directly connected to the mechanical arm end 1031 is, for example, the first tracker 106, and the tracker indirectly connected to the mechanical arm end 1031 is, for example, the second tracker 107.

Figure 7:
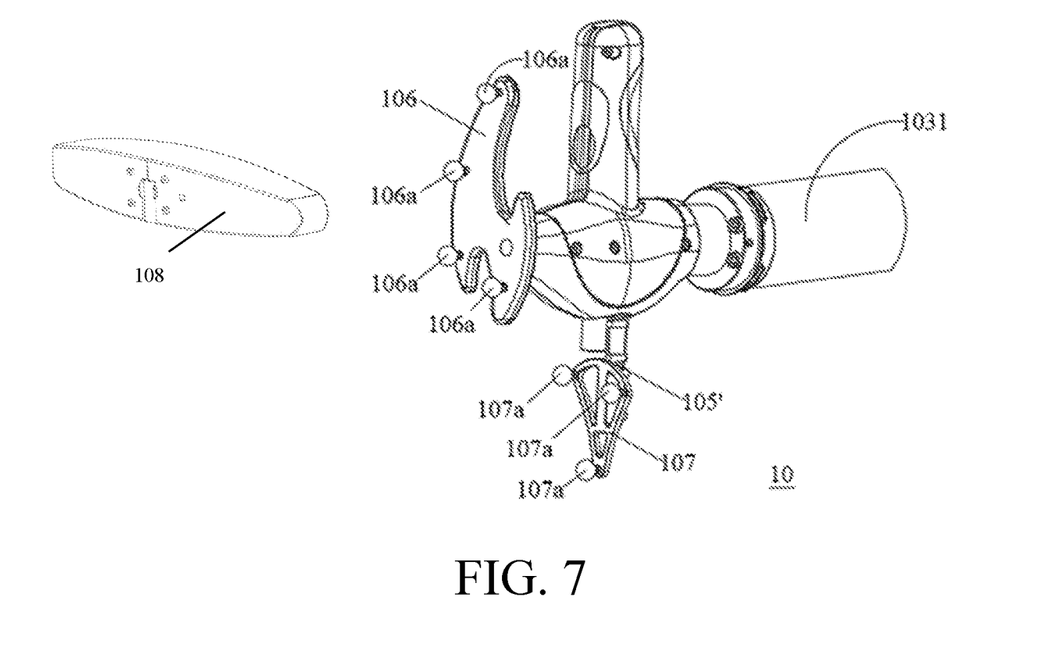
FIG. 7 is a schematic structural diagram of a surgical system according to an embodiment of the present application.

In some embodiments, the first tracker and the second tracker are both optical trackers, the first tracker is provided with a first preset marker, and the second tracker is provided with a second preset marker. As shown in FIG. 7, by way of example, the first tracker 106 is provided with a plurality of first preset markers 106a, and the second tracker 107 is provided with a plurality of second preset markers 107a. The first preset marker 106a and the second preset marker 107a may be, for example, reflective balls, active Light Emitting Diodes (LEDs), or any markers that can be tracked by the localizer 108. It should be noted that, the number of the first preset markers on the first tracker 106 can be flexibly adjusted according to the actual situation, which is not limited in the present application. Similarly, the number of the second preset markers on the second tracker 107 can also be flexibly adjusted according to the actual situation, which is not limited in the present application either.

The plurality of first preset markers 106*a* may define a spatial three-dimensional coordinate system where the first tracker 106 is located, which is referred to as a first tracker coordinate system. Likewise, the plurality of second preset markers 107*a* may define a spatial three-dimensional coordinate system where the second tracker 107 is located, which is referred to as a second tracker coordinate system. The localizer 108 may collect images of the first preset markers 106*a* and the second preset markers 107*a*, and according to positions of the first preset markers 106*a* and of the second preset markers 107*a* in the images, the spatial positions of the first preset markers 106*a* and the second preset markers 107*a* may be determined, and then, the position of the first tracker coordinate system in the absolute coordinate system and the position of the second tracker coordinate system in the absolute coordinate system can be determined.

Exemplarily, the localizer 108 may be a binocular vision image positioning system, and specifically, can determine the spatial positions of the first preset markers 106*a* and the second preset markers 107*a* according to parallax principle, and then can determine the position of the first tracker coordinate system in the absolute coordinate system and the position of the second tracker coordinate system in the absolute coordinate system.

The plane on which the moving path of the mechanical arm end 1031 is located is coincident with or parallel to the plane on which the moving path of the first tracker 106 is located, and an angular relationship between the planes are considered during calibration. Therefore, in practical applications, the position of the plane on which the moving path of the first tracker 106 is located in the absolute coordinate system can be used to represent the position of the plane on which the moving path of the mechanical arm end 1031 is located in the absolute coordinate system. That is to say, in step S102, the first position can be obtained only by determining the position of the plane on which the moving path of the first tracker 106 is located in the absolute coordinate system. Similarly, the position of the plane on which the moving path of the second tracker 107 is located in the absolute coordinate system can also be used to represent the position of the plane on which the moving path of the mechanical arm end 1031 is located in the absolute coordinate system. In step S102, it is only necessary to determine the position of the plane on which the moving path of the second tracker 107 is located in the absolute coordinate system, to obtain the first position.

In some embodiments, the first position may be angular position information of a plane defined by the moving path. That is, the first position may be an angle of the plane defined by the moving path relative to a reference plane in the absolute coordinate system.

The method further includes step S103, obtaining a second position of the target feature structure in the absolute coordinate system.

In some embodiments, for example, the second position of the target feature structure in the absolute coordinate system may be obtained by tracking a tracker positioned on the target feature structure by means of a localizer. As shown in FIG. 7, for example, the second tracker 107 positioned on the target feature structure 105' may be tracked by the localizer 108 to obtain the second position of the target feature structure 105' in the absolute coordinate system.

In some embodiments, the second position may be angular position information of a predetermined plane of the target feature structure. That is, the second position may be an angle of the predetermined plane of the target feature structure relative to the reference plane in the absolute coordinate system. Assuming that the target feature structure is a medical device, the predetermined plane of the target feature structure may include a first surface of the medical device, the first surface may be an upper surface or a lower surface of the medical device, which can be flexibly adjusted according to a target plane, and the present application is not limited thereto. For example, when the target plane is an osteotomy plane, the first surface may be a surface (e.g., the lower surface) of the saw blade close to the osteotomy plane. In another example, the target plane is a plane defined by adding the thickness of the saw blade on the osteotomy plane, and the first surface may be a surface (e.g., the upper surface) of the saw blade away from the osteotomy plane.

Specifically, the step S103 may include steps S1031 and S1032.

In the step S1031, a fourth position of the second tracker coordinate system in the absolute coordinate system is obtained. Exemplarily, the position of the second tracker coordinate system in the absolute coordinate system can be determined according to the localizer 108 and the second preset markers 107*a* and is referred to as the fourth position here for the convenience of distinction. The absolute coordinate system may be a world coordinate system or a camera coordinate system where the localizer 108 is located, and the present application is not limited for this aspect.

In the step S1032, angular position information of the predetermined plane in the absolute coordinate system is determined according to the fourth position and a predetermined fifth position of the predetermined plane in the second tracker coordinate system. Specifically, after the installation of the second tracker 107 is completed, the physical positional relationship between the second tracker 107 and the target feature structure 105' can be determined, and thus, the fifth position of the predetermined plane of the target feature structure 105' in the second tracker coordinate system can also be determined. Therefore, according to the fourth position of the second tracker coordinate system in the absolute coordinate system and the fifth position of the predetermined plane in the second tracker coordinate system, the angular position information of the predetermined plane in the absolute coordinate system can be determined.

In the embodiments of the present application, the localizer 108 can continuously obtain the position information of the second tracker 107 during the movement of the mechanical arm end 1031 along the predetermined path. The above-mentioned angular position information of the predetermined plane in the absolute coordinate system may be the angular position information of the predetermined plane in the absolute coordinate system when the mechanical arm end 1031 is located at a certain position on the moving path, or may be a mean value of multiple angular position information of the predetermined plane in the absolute coordinate system when the mechanical arm end 1031 is located at multiple positions on the moving path. That is, the second position includes the angular position information of the predetermined plane in the absolute coordinate system corresponding to the first position point, and the first position point is one of the position points on the moving path of the mechanical arm end 1031; or, the second position includes the mean value of the multiple angular position information of the predetermined plane in the absolute coordinate system corresponding to the plurality of first position points.

The method further includes step S104, determining a relative positional relationship between the target feature structure and the mechanical arm end coordinate system according to the first position, the second position and a predetermined third position of the moving path in the mechanical arm end coordinate system.

In some embodiments, the step S104 may specifically include steps S1041 and S1042 described as below.

In the step S1041, a relative positional relationship between the plane where the moving path is located and the predetermined plane of the target feature structure is determined according to the first position and the second position. Specifically, according to the angular position information of the plane where the moving path is located in the absolute coordinate system and the angular position information of the predetermined plane of the target feature structure in the absolute coordinate system, for example, an angle between the plane where the moving path is located and the predetermined plane can be determined.

In the step S1042, the relative positional relationship between the target feature structure and the mechanical arm end coordinate system is determined, according to the relative positional relationship between the plane where the moving path is located and the predetermined plane of the target feature structure, and the third position of the moving path in the mechanical arm end coordinate system. In some embodiments, the relative positional relationship between the target feature structure and the mechanical arm end coordinate system may be relative angular position information of the predetermined plane of the target feature structure and the mechanical arm end coordinate system.

As shown in FIG. 5, for example, P1 is a plane where the preset moving path is located (a plane defined by the moving path), and P2 is a reference plane. The third position of the moving path in the mechanical arm end coordinate system, that is, the position of the plane P1 where the moving path is located in the mechanical arm end coordinate system can be predetermined. Exemplarily, when setting the moving path, for example, the plane where the X axis and Z axis of the mechanical arm end coordinate system are located, may be set as the plane P1 where the moving path is located. Therefore, according to the relative positional relationship between the plane where the moving path is located and the predetermined plane of the target feature structure, and the position of the plane where the moving path is located in the mechanical arm end coordinate system, the relative angular position information of the predetermined plane of the target feature structure and the mechanical arm end coordinate system can be determined.

In order to facilitate the operation of the surgery, in some embodiments, the second tracker 107 is detachably connected to the target feature structure 105', for example, the second tracker 107 can clamp the target feature structure 105' by a clamping member on the second tracker 107. After the step S104 is completed, the second tracker 107 can be removed from the target feature structure 105', so as to avoid the normal operation of the target feature structure 105' from being affected.

Based on the calibration method provided by the foregoing embodiments, correspondingly, the embodiments of the present application further provide specific implementations of the mechanical arm control method.

Figure 8:
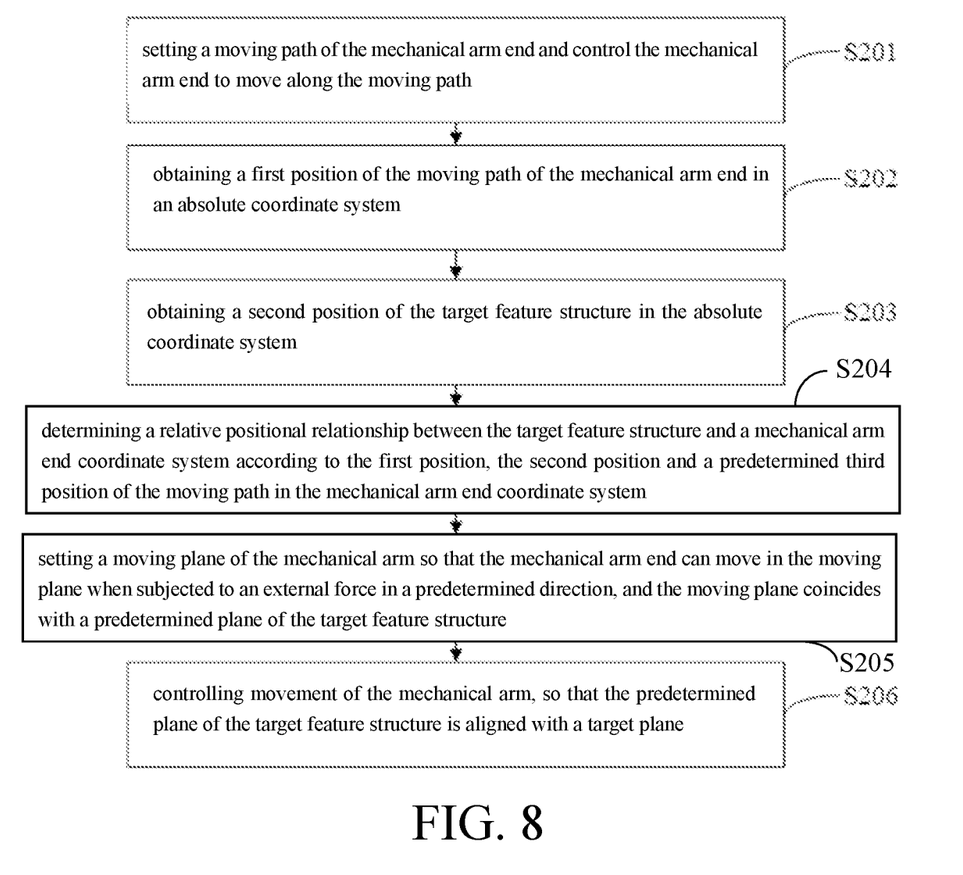
FIG. 8 is a schematic flowchart of a calibration method provided by an embodiment of the present application.

As shown in FIG. 8, the mechanical arm control method provided by the embodiments of the present application comprises the following steps:

S201, setting a moving path of the mechanical arm end and controlling the mechanical arm end to move along the moving path;

S202, obtaining a first position of the moving path of the mechanical arm end in an absolute coordinate system;

S203, obtaining a second position of the target feature structure in the absolute coordinate system;

S204, determining a relative positional relationship between the target feature structure and a mechanical arm end coordinate system, according to the first position, the second position and a predetermined third position of the moving path in the mechanical arm end coordinate system;

S205, setting a moving plane of the mechanical arm so that the mechanical arm end can move in the moving plane when subjected to an external force in a predetermined direction, and the moving plane coincides with a predetermined plane of the target feature structure; that is, setting a plane on which the mechanical arm end can move freely, so that the plane where the mechanical arm end can move freely coincides with the predetermined plane; and S206, controlling movement of the mechanical arm, so that the predetermined plane of the target feature structure is aligned with a target plane. Specifically, the mechanical arm can be controlled to move so that the predetermined plane of the target feature structure coincides with the preset target plane. Since the moving plane of the mechanical arm end coincides with the predetermined plane, the moving plane of the mechanical arm end and the predetermined plane of the target feature structure can be consistent with the target plane, and no angle error is generated, thereby ensuring the surgical accuracy and improving the surgical effect.

It should be noted that the specific processes of steps S201 to S204 are the same as those of steps S101 to S104, which will not be repeated here for the sake of brevity of description.

Figure 9:
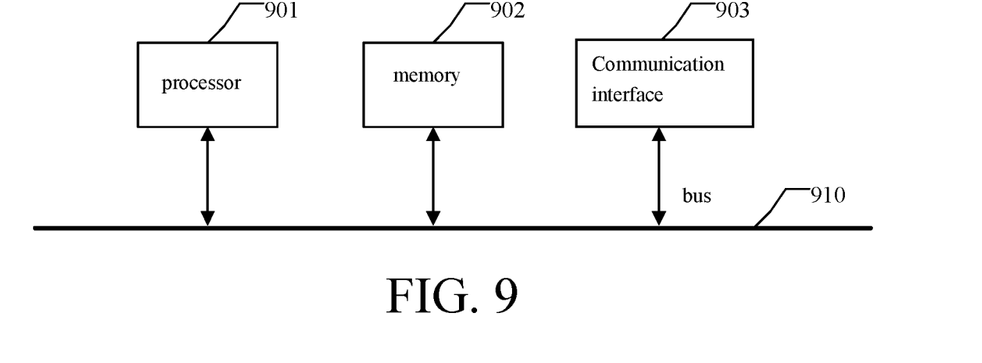
FIG. 9 is a schematic structural diagram of a controller according to an embodiment of the present application.

As mentioned above, the controller in the surgical system 10 provided in the embodiments of the present application may be used to perform the calibration method or the mechanical arm control method of the embodiments of the present application. Specifically, as shown in FIG. 9, the controller may include a processor 901, a memory 902, and a computer program stored in the memory 902 which can be executed on the processor, and when the computer program is executed by the processor 901, the steps of the above-mentioned calibration method or the mechanical arm control method can be performed.

Specifically, in some embodiments, the controller can set a moving path of the mechanical arm and control the mechanical arm end to move along the moving path, and the moving path includes at least three position points that are not located on a same straight line; based on an obtained first position of the moving path of the mechanical arm end in an absolute coordinate system, an obtained second position of the target feature structure in the absolute coordinate system, and a predetermined third position of the moving path in a mechanical arm end coordinate system, a relative positional relationship between the target feature structure and the mechanical arm end coordinate system can be determined.

Specifically, in some other embodiments, the controller further can set a moving path of the mechanical arm end and control the mechanical arm end to move along the moving path, wherein the moving path includes at least three position points that are not located on a same straight line; the controller can determine a relative positional relationship of the target feature structure and a mechanical arm end coordinate system based on an obtained first position of the moving path of the mechanical arm end in an absolute coordinate system, an obtained second position of the target feature structure in the absolute coordinate system, and a predetermined third position of the moving path in the mechanical arm end coordinate system; the controller can set a moving plane of the mechanical arm, so that the mechanical arm end can move in the moving plane when subjected to an external force in a predetermined direction, wherein the moving plane coincides with a predetermined plane of the target feature structure; and the controller can control the mechanical arm to move so as to align the predetermined plane of the target feature structure with a target plane.

In some embodiments, the relative positional relationship between the target feature structure and the mechanical arm end coordinate system is relative angular position information of the predetermined plane of the target feature structure and the mechanical arm end coordinate system.

In some embodiments, the first position is angular position information of a plane defined by the moving path; the second position is angular position information of the predetermined plane of the target feature structure.

In the embodiments of the present application, the above-mentioned processor 901 may include a Central Processing Unit (CPU), or an Application Specific Integrated Circuit (ASIC), or may be configured as one or more integrated circuits for implementing the embodiments of the present application.

The memory 902 may include mass storage for data or instructions. By way of example and not limitation, the memory 902 may include a Hard Disk Drive (HDD), a floppy disk drive, a flash memory, an optical disk, a magneto-optical disk, a magnetic tape, a Universal Serial Bus (USB) drive, or a combination of two or more of the above. In one example, the memory 902 may include removable or non-removable (or fixed) media, or the memory 902 may be a non-volatile solid-state memory. The memory 902 may be internal or external to an integrated gateway disaster recovery device.

In one example, the memory 902 may be a Read Only Memory (ROM). In one example, the ROM may be a mask programmed ROM, a programmable ROM (PROM), an erasable PROM (EPROM), an electrically erasable PROM (EEPROM), an electrically rewritable ROM (EAROM), a flash memory, or a combination of two or more of the above.

The memory 902 may include a read only memory (ROM), a random access memory (RAM), a magnetic disk storage media device, an optical storage media device, a flash memory device, an electrical, optical or other physical/tangible memory storage device. Thus, typically, the memory includes one or more tangible (non-transitory) computer-readable storage media (e.g., memory device) encoded with software including computer-executable instructions, and when the software is executed (e.g., by one or more processors), it is operable to perform the operations described with reference to a method according to one aspect of the present application.

By reading and executing the computer program instructions stored in the memory 902, the processor 901 can implement the method/steps S101 to S104 of the embodiment as shown in FIG. 4 or the method/steps S201 to S206 of the embodiment as shown in FIG. 8, and achieve the corresponding technical effects by executing the method/steps of the embodiment as shown in FIG. 4 or FIG. 8, which are not repeated here for the sake of brevity.

In one example, the electronic device may further include a communication interface 903 and a bus 910. As shown in FIG. 9, the processor 901, the memory 902, and the communication interface 903 are connected and communicated with each other through the bus 910.

The communication interface 903 is mainly adapted to achieve the communication between modules, apparatuses, units and/or devices in the embodiments of the present application.

The bus 910 includes a hardware, a software, or both, and couples components of the electronic device to each other. By way of example and not limitation, the bus may include an Accelerated Graphics Port (AGP) or other graphics bus, an Extended Industry Standard Architecture (EISA) bus, a Front Side Bus (FSB), a Hyper Transport (HT) interconnect, an Industry Standard Architecture (ISA) bus, an unlimited bandwidth interconnect, a Low Pin Count (LPC) bus, a memory bus, a Micro Channel Architecture (MCA) bus, a Peripheral Component Interconnect (PCI) bus, a PCI-Express (PCI-X) bus, a Serial Advanced Technology Attachment (SATA) bus, a Video Electronics Standards Association Local (VLB) bus or other suitable bus, or a combination of two or more of the above. The bus 910 may include one or more buses, where appropriate. Although the embodiments of the present application describe and illustrate a particular bus, the present application contemplates any suitable bus or interconnect.

Various modules/units in the system shown in FIG. 3 have functions of implementing various steps in FIG. 4 or FIG. 8, and can achieve the corresponding technical effects, which are not repeated here for the sake of concise description.

Further, in combination with the calibration method and the mechanical arm control method in the foregoing embodiments, the embodiments of the present application may provide a computer-readable storage medium for implementation. The computer program instructions are stored on the computer-readable storage medium; and when the computer program instructions are executed by the processor, any one of the plane calibration methods in the foregoing embodiments is implemented. Examples of computer-readable storage media include non-transitory computer-readable storage media such as an electronic circuit, a semiconductor memory device, a ROM, a random access memory, a flash memory, an erasable ROM (EROM), a floppy disk, a CD-ROM, an optical disk, and a hard disk.

In the present embodiment, a computer program product is further provided, wherein the program product is stored in a non-volatile storage medium, and the program product is executed by at least one processor to implement the steps of the above-mentioned calibration method or the mechanical arm control method.

The computer program product (also referred to as a program, software, software application, script, or code) may be written in any form of programming language, including compiled or interpreted languages, and the computer program may be deployed in any form, including a stand-alone program or a module, component, subroutine, or other unit suitable for use in a computing environment. The computer program does not necessarily correspond to a file in a file system. The program may be stored in sections of files that hold other programs or data (such as one or more scripts stored in a markup language document), in a single file dedicated to the program being described, or in multiple collaborative files (for example, a file that stores one or more modules, subroutines, or portions of code). The computer program can be deployed to be executed on one computer, or on multiple computers located at one site or distributed at multiple sites and interconnected by a communication network.

It shall be understood that the present application is not limited to the specific configurations and processes described above and illustrated in the figures. For the sake of brevity, detailed descriptions of known methods are omitted here. In the above-described embodiments, several specific steps are described and shown as examples. However, the method process of the present application is not limited to the specific steps described and shown, and the person skilled in the art can make various changes, modifications and additions, or change the sequence of steps after comprehending the spirit of the present application.

The functional blocks shown in the above structural block diagrams may be implemented as hardware, software, firmware or a combination thereof. When implemented in hardware, the functional blocks can be, for example, electronic circuits, Application Specific Integrated Circuits (ASICs), appropriate firmware, plug-ins, feature cards, etc. When implemented in software, elements of the present application are programs or code segments used to perform the required tasks. The program or code segments may be stored in a machine-readable medium or transmitted over a transmission medium or communication link by a data signal carried in a carrier wave. The "machine-readable medium" may include any medium that can store or transmit information. Examples of the machine-readable media include electronic circuits, semiconductor memory devices, ROMs, flash memories, erasable ROMs (EROMs), floppy disks, CD-ROMs, optical disks, hard disks, fiber optic media, Radio Frequency (RF) links, etc. The code segments may be downloaded via a computer network such as the Internet, an intranet, or the like.

It should further be noted that the exemplary embodiments mentioned in the present application describe some methods or systems based on a series of steps or devices. However, the present application is not limited to the order of the above steps, that is, the steps may be performed in the order mentioned in the embodiments, or may be performed in the order different from that in the embodiments, or several steps may be performed simultaneously.

Aspects of the present application are described above with reference to flowchart illustrations and/or block diagrams of methods, apparatus (systems) and computer program products according to embodiments of the present application. It shall be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine such that execution of the instructions via the processor of the computer or other programmable data processing apparatus enables the implementation of the functions/acts specified in one or more blocks of the flowchart and/or block diagrams. Such processor may be, but are not limited to, a general purpose processor, a special purpose processor, an application specific processor, or a field programmable logic circuit. It can also be understood that each block of the block diagrams and/or flowchart illustrations, and combinations of blocks in the block diagrams and/or flowchart illustrations, can further be implemented by special purpose hardware for performing the specified functions or actions, or by a combination of special purpose hardware and/or computer instructions.

The above contents are only the specific embodiments of the present application, the person skilled in the art can clearly understand that, the concrete working process of the system, module and unit described above can be implemented with reference to the corresponding process in the above-mentioned embodiments of methods, which are not repeated here for the convenience and conciseness of description. It should be understood that the protection scope of the present application is not limited to this. Any person skilled in the art can easily think of various equivalent modifications or replacements within the technical scope disclosed in the present application, and these modifications or replacements should all fall within the protection scope of the present application.

What is claimed is:

1. A calibration method for calibrating an angle of a target feature structure installed on an end of a mechanical arm, the method comprising steps of:
   setting a moving path of the end and controlling the end to move along the moving path, the moving path comprising at least three position points that are not located on a same straight line while are located on a same plane, wherein a single plane is defined by the moving path;
   obtaining angular position information of the single plane defined by the moving path in the absolute coordinate system;
   obtaining angular position information of a predetermined plane of the target feature structure in the absolute coordinate system; and
   determining a relative angular positional relationship between the predetermined plane of the target feature structure and a mechanical arm end coordinate system according to the angular position information of the single plane defined by the moving path in the absolute coordinate system, the angular position information of the predetermined plane of the target feature structure in the absolute coordinate system, and a predetermined angular position information of the single plane defined by the moving path in the mechanical arm end coordinate system.

2. The calibration method according to claim 1, wherein the moving path comprises a polyline path or a curved path.

3. The calibration method according to claim 1, wherein the step of obtaining the angular position information of the single plane defined by the moving path in the absolute coordinate system specifically comprises a step of:
   tracking a tracker directly or indirectly connected to the end by a localizer to obtain the angular position information of the single plane defined by the moving path in the absolute coordinate system, wherein the localizer is adapted to collect images of markers on the tracker and obtain spatial orientation information of the tracker according to positions of the markers in the images.

4. The calibration method according to claim 3, wherein the tracker is a tracker disposed on the target feature structure.

5. The calibration method according to claim 3, wherein the tracker is an optical tracker.

6. A mechanical arm control method using the calibration method according to claim 3, the control method is adapted to control a predetermined plane of the target feature structure installed on the end of the mechanical arm to align with a target plane, the control method comprises steps of:

calibrating an angle between the target feature structure and the end by the calibration method;

setting a moving plane of the mechanical arm, so that the end can move in the moving plane when subjected to an external force in a predetermined direction, and the moving plane coincides with the predetermined plane of the target feature structure; and controlling the mechanical arm to move so as to align the predetermined plane with the target plane.

7. The mechanical arm control method according to claim 6, wherein the tracker is a tracker disposed on the target feature structure.

8. The mechanical arm control method according to claim 6, wherein the step of obtaining the angular position information of the predetermined plane of the target feature structure in the absolute coordinate system specifically comprises a step of: tracking the tracker positioned on the target feature structure by the localizer to obtain the angular position information of the predetermined plane of the target feature structure in the absolute coordinate system, wherein the localizer is adapted to collect images of markers on the tracker and obtain spatial orientation information of the tracker according to positions of the markers in the images.

9. The mechanical arm control method according to claim 6, wherein the tracker is an optical tracker.

10. The calibration method according to claim 1, wherein the step of obtaining the angular position information of the predetermined plane of the target feature structure in the absolute coordinate system specifically comprises a step of: tracking a tracker positioned on the target feature structure by a localizer to obtain the angular position information of the predetermined plane of the target feature structure in the absolute coordinate system, wherein the localizer is adapted to collect images of markers on the tracker and obtain spatial orientation information of the tracker according to positions of the markers in the images.

11. A surgical system comprising:

a mechanical arm, an end of the mechanical arm being installed with a target feature structure; and a controller, programmed to:

set a moving path of the end and control the end to move along the moving path, the moving path comprising at least three position points that are not located on a same straight line while are located on a same plane, wherein a single plane is defined by the moving path; and determine a relative angular positional relationship between a predetermined plane of the target feature structure and a mechanical arm end coordinate system based on an obtained angular position information of the single plane defined by the moving path in an absolute coordinate system, an obtained angular position information of the predetermined plane of the target feature structure in the absolute coordinate system and a predetermined angular position information of the single plane defined by the moving path in the mechanical arm end coordinate system.

* * * * *